United States Patent
Bean

(10) Patent No.: US 8,277,748 B2
(45) Date of Patent: Oct. 2, 2012

(54) CONTAINER FOR WASHER OR AUTOCLAVE

(75) Inventor: Douglas Colin Bean, Wantirna South (AU)

(73) Assignee: Douglas Bean (Australia) Pty Ltd, Wantirna South (AU)

( * ) Notice: Subject to any disclaimer, the term of this patent is extended or adjusted under 35 U.S.C. 154(b) by 4 days.

(21) Appl. No.: 12/667,012

(22) PCT Filed: Jun. 30, 2008

(86) PCT No.: PCT/AU2008/000956
§ 371 (c)(1),
(2), (4) Date: Jun. 14, 2010

(87) PCT Pub. No.: WO2009/003227
PCT Pub. Date: Jan. 8, 2009

(65) Prior Publication Data
US 2010/0278689 A1    Nov. 4, 2010

(30) Foreign Application Priority Data

Jun. 29, 2007  (AU) ............................. 2007903573

(51) Int. Cl.
*A61L 2/00* (2006.01)
*B65D 6/10* (2006.01)
(52) U.S. Cl. ......... 422/300; 422/297; 206/307; 206/438
(58) Field of Classification Search .................... 422/28, 422/292, 300, 297; 206/370, 438
See application file for complete search history.

(56) References Cited

U.S. PATENT DOCUMENTS

| | | | |
|---|---|---|---|
| 5,441,709 A | 8/1995 | Berry, Jr. | |
| 5,720,930 A * | 2/1998 | Bean | 422/300 |
| 5,725,097 A | 3/1998 | Bettenhausen et al. | |
| 5,766,561 A * | 6/1998 | Frieze et al. | 422/297 |
| 6,048,503 A | 4/2000 | Riley | |
| 6,048,504 A * | 4/2000 | Riley | 422/300 |
| 6,217,835 B1 | 4/2001 | Riley et al. | |

FOREIGN PATENT DOCUMENTS

| | | |
|---|---|---|
| AU | 24396/95 | 10/1997 |
| CN | 1362047 | 8/2002 |
| WO | WO 95/31222 | 11/1995 |
| WO | WO 99/49903 | 10/1999 |
| WO | WO 00/12142 | 3/2000 |
| WO | WO 2009/003227 | 1/2009 |

OTHER PUBLICATIONS

PCT International Search Report, PCT/AU2008/00956 dated Oct. 3, 2009.

* cited by examiner

*Primary Examiner* — Sean E Conley
(74) *Attorney, Agent, or Firm* — TraskBritt

(57) ABSTRACT

A container for enabling fluid flow therethrough for cleaning or sterilizing of the contents, comprises a tray (10) and lid (20) and having respective bases (11, 21) and side walls (17, 27). The bases (11, 21) have perforations (12, 22) defined by elliptically shaped perforation walls (13, 23) with their major axes vertical to allow easy flow of the cleaning fluid through the container and minimum contact points with the contents or other containers. The internal corners (30) of the perforations (12, 22) in horizontal sections are smoothly curved to minimize debris or deposits collecting and resisting removal. A method of cleaning or sterilizing using the container is also described.

6 Claims, 4 Drawing Sheets

CONTAINER FOR WASHER OR AUTOCLAVE

CROSS-REFERENCE TO RELATED APPLICATION

This application is a U.S. national entry under 35 U.S.C. §371 of International Application No. PCT/AU2008/000956, filed 30 Jun. 2008, published in English as PCT International Publication No. WO 2009/003227 A1 on 8 Jan. 2009 which is based upon and claims the priority of Australian Patent Application No. 2007903573 filed 29 Jun. 2007. The entire contents of these applications and their associated specifications are incorporated herein by this cross-reference.

TECHNICAL FIELD

This invention relates to a container component for enabling fluid flow therethrough for cleaning or sterilising of the contents within the container and further relates to a method of cleaning or sterilising the contents within a container.

BACKGROUND

In medical and dental establishments, because of environmental problems and the cost and difficulty of burning and dumping of medical waste, there is a growing tendency to return to reusable products. For example medical and dental instruments after use are frequently returned in a container to a washing or sterilising facility where the instruments are decontaminated. The instruments can then be safely handled without risk from infections such as HIV and Hepatitis caused by inadvertent cutting or puncturing of the person handling a contaminated instrument. The instrument can be cleaned and serviced as necessary and sterilisation in an autoclave follows, usually with porous filter medium surrounding the tray or other container holding the instruments. The instruments while remaining protected by the porous wrapping are then stored and subsequently returned to the surgery for reuse by the dentist or doctor.

Trays made of stainless steel and synthetic materials are known for holding dental and medical instruments for sterilisation in an autoclave. Such stainless steel trays have a base made of a sheet of flat stainless steel material which has an array of cylindrical holes drilled through the base to allow steam in the autoclave to pass through the base. However such stainless and synthetic steel trays are expensive and/or may not allow steam or washing liquid to reach all parts of the instruments resting on them.

Australian Patent Specification No. AU-24539/88 discloses an autoclave container in the form of a tray made of a plastics material, the tray having a base with perforations defined by walls, the walls progressively widening from a top point to a flat bottom surface of the base. The flat bottom surface enables a substantial amount of the heat stored within the plastics material after the tray has been an autoclave to be yielded up through the flat base surface and thereby help evaporate any moisture, such as condensation, particularly within the filter material placed around the tray when in the autoclave. However the tray in this patent specification would not be particularly effective in a washer where water jets are directed upwardly against the base of the tray, since the large flat bottom surface area would deflect much of the water downwardly rather than allowing the water to pass upwardly through the perforations to reach the instruments in the tray.

A type of closed autoclave vessel frequently used in hospitals for holding instruments to be sterilised in an autoclave has a square bottom of about 40 cm width and which has a perforated central opening, e.g. having a diameter of about 10 cm. The circular central opening in use is covered by a permeable filter material. The lid of the vessel is similarly constructed, having a 10 cm diameter circular perforated opening in the centre of the lid covered in use by a permeable filter. Inside the closed vessel there can be a tray which is perforated and which supports the instruments to be sterilised. Steam flows through the upper circular opening in the lid to reach the interior of the vessel and passes out through the lower central perforated opening. The flow of steam through such a vessel tends to be greatest in the central region of the space enclosed within the vessel, this effect being the result of the steam flowing through a path of least resistance. Hence it is possible that the outer sides and particularly the corners of the vessel may be inadequately heated to effectively sterilise the instruments at the edges or in the corners of the vessel.

Australian Patent Specification No. AU-24396/95 (Patent No. 682770) discloses a container component for enabling cleaning of articles by fluid flow therethrough, the component having a base with perforations defined by intersecting perforation walls. Each of the walls in vertical cross section has a narrow top, widens in a downwards direction to a maximum width, and then narrows again to a narrow bottom. The preferred cross sectional shape of the perforation walls is elliptical with the major axis of the ellipse being upright. This container component, and also the tray disclosed in AU-24539/88, has many locations such as corners or crevices where small quantities of blood, debris, or other deposits or contaminants can be lodged and can be difficult to completely remove during the cleaning process. Such deposits can later contaminate instruments or other articles stored within the container component, or can dislodge in a surgery or other environment where all possible sources of contamination are desirably excluded. Even if the deposits are sterilised during the cleaning operation which the container component and instruments or articles carried thereby undergo, nevertheless the deposits are an undesirable potential source of particulate contamination in surgery, dental procedure, etc.

It is an object of the present invention in a first aspect to provide a container component for enabling fluid flow therethrough for effective cleaning of contents of the container with reduced risk of contaminants or deposits lodging or remaining in the container component.

It is a preferred object of the present invention to provide a container component suitable for placement within a washer in which washing liquid is directed upwardly and/or downwardly so as to pass through the container component thereby washing articles in the container and removing any contaminants or deposits in or on the container component.

It is a further preferred object of the present invention to provide a container component suitable for use in an autoclave and enabling steam to flow through the container component for effective sterilisation of articles in the container and removing any contaminants or deposits in or on the container component.

It is an object of the present invention in a second aspect to provide a method for cleaning or sterilising articles located within a container having a container component enabling a fluid flow therethrough with reduced risk of contaminants or deposits lodging or remaining in or on the container component.

SUMMARY OF INVENTION

According to the first aspect of the invention there is provided a container component for enabling cleaning of articles located within the container component by fluid flow through the component, comprising a base, the base having perforations provided over substantially the entire area where the articles are in use located and through which the cleaning fluid can flow, the perforations in the base being defined by perforation walls, each of the walls in vertical cross section having a narrow top, widening in a downwards direction to a maximum width and then narrowing again to a narrow bottom, the maximum width being less than the distance from the top to the bottom, wherein the perforation walls include longitudinal perforation walls extending in a first direction and transverse perforation walls extending in a different second direction so that the longitudinal and transverse perforation walls meet at intersections defining corners of the perforations, and wherein the internal corners are smoothly rounded so that there is no sharp internal angle formed where the longitudinal and transverse perforation walls meet.

Terms used in the specification, including claims, which may normally mean or at least imply some particular orientation are used for convenience and do not limit the invention to the particular implied orientation. For example, the term "base", although normally implying a bottom or lower position, nevertheless could comprise a top or covering component, e.g. in the case of the container component comprising a lid of an autoclavable instrument tray in which the "base" would comprise the top wall of the container. In another example, the term "horizontal" in reference to the cross-sections through the intersections is not to be interpreted to necessarily mean that the base is a horizontal planar base since the base may, for example, comprise an upright side wall of the container component. Likewise other orientation terms such as "vertical", "top" "downwards", "bottom" are not to be interpreted literally and narrowly but are to be interpreted as relative orientational terms.

The radius of curvature of each internal corner may progressively increase in successive horizontal cross-sections through the respective intersections starting from cross sections near the tops of the walls and progressing towards cross sections approaching and at the maximum width of the walls.

Preferably the curvature of the internal corners of the perforations in the horizontal plane where the walls reach their maximum width is greater than the curvature of the internal corners of the perforations at any other horizontal cross-section.

In one possible embodiment of the container component, each intersection in any one of multiple horizontal cross-sections therethrough is of generally cruciform shape. The term "cruciform shape" is not to be interpreted narrowly to necessarily refer only to a shape in which the longitudinal and transverse perforation walls intersect at substantially 90° to each other. The expression is intended merely to indicate that the longitudinal and transverse perforation walls intersect and cross each other and, for example, the crossings could be at angles other than 90° e.g. at a 60° internal angle so as to also define internal corners with an internal angle of about 120°.

In one embodiment suitable for medical or dental instrument containers each of the internal corners of the perforations in the horizontal plane where the walls reach their maximum width may have a radius of curvature of about 1 mm or greater.

In one preferred embodiment, the component comprises a tray, the base of the component defining a bottom of the tray, a plurality of side portions being located around the perimeter of the base, the perforations in the base being provided over substantially the entire surface area out to the perimeter where the side portions are located, so that the articles to be cleaned are located by the side portions entirely within the perimeter of the base where the perforations are provided, the tray having an open top through which the cleaning fluid can flow, wherein the perforation walls have terminal ends which meet and join with the side portions, and wherein a horizontal cross-section through each meeting of the terminal end of a perforation wall with the side portion is generally of T-shape and the internal corners of the T-shape are smoothly rounded so that there is no sharp internal angle formed where the perforation wall meets with the side portion.

The container component may be made of a plastics material, particularly in the case of use in sterilising operations being a material capable of withstanding autoclave temperatures. A preferred material is polypropylene.

According to the second aspect of the invention there is provided a method of cleaning or sterilising articles comprising the steps of:

providing a container component for receiving the articles during the cleaning or sterilising process, the container component comprising a base, the base having perforations;

locating the articles to be cleaned or sterilised within the container component so that they are located within an area where the base has the perforations provided therein; and causing a cleaning or sterilising fluid to flow past the articles within the container component including passing through the perforations of the base throughout substantially the entire area where the articles are located, wherein the perforations in the base are defined by perforation walls, each of the walls in vertical cross section having a narrow top, widening in a downwards direction to a maximum width and then narrowing again to a narrow bottom, the maximum width being less than the distance from the top to the bottom, wherein the perforation walls include longitudinal perforation walls extending in a first direction and transverse perforation walls extending in a different second direction so that the longitudinal and transverse perforation walls meet at intersections defining corners of the perforations, and wherein the internal corners are smoothly rounded so that there is no sharp internal angle formed where the longitudinal and transverse perforation walls meet.

Further preferred features of the container component used in the method according to the second aspect of the invention can be substantially as described above in connection with the first aspect of the invention.

BRIEF DESCRIPTION OF DRAWINGS

Possible and preferred features of the present invention will now be described with particular reference to the accompanying drawings. In the drawings.

DETAILED DESCRIPTION

Figure 1:
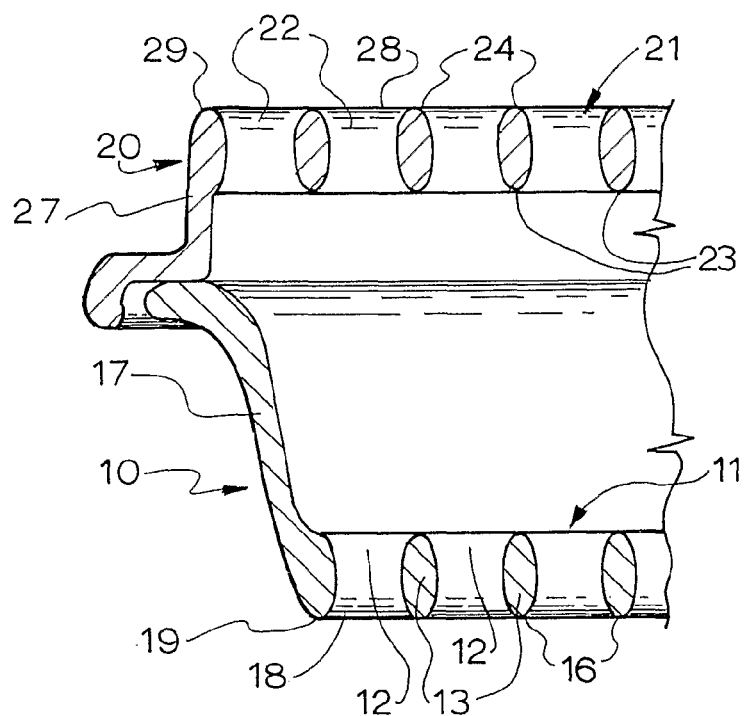
FIG. 1 shows a cross-section through a fragment of a container having a tray and a lid both embodying the present invention.

The two part container shown in FIG. 1 comprises a tray 10 and a cover or lid 20 each of which embodies the present invention. However the invention also relates to simple open topped trays such as the tray 10, e.g. for holding dental instruments to be placed in a washing apparatus where washing water containing disinfectant is directed in multiple directions within the washer so as to pass through the tray and wash the articles in the tray.

The tray 10 includes a base 11. Similarly the lid 20 has a base 21. The base 11 has perforations 12 and similarly the lid 20 has perforations 22 to allow cleaning fluid, such as water in a washer or steam in an autoclave, to pass through the base 11 or 21 to contact articles received within the tray 10.

The tray 10 and lid 20 can be moulded from plastics material such as polypropylene capable of withstanding autoclave temperatures.

The tray 10 has a side wall 17 extending upwardly from the perimeter or edge of the perforated base 11, and the lid 20 has side wall 27 having a complementary shape at its edge to the top of the side wall 17 to enable the lid 20 to fit to the tray 10.

Figure 2:
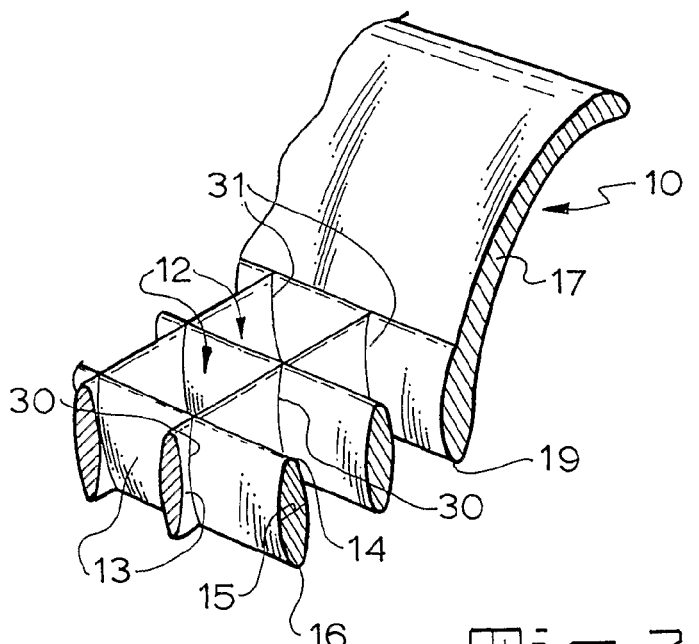
FIG. 2 shows a fragmentary perspective sectional view of a portion of a previously known container component.
Figure 3:
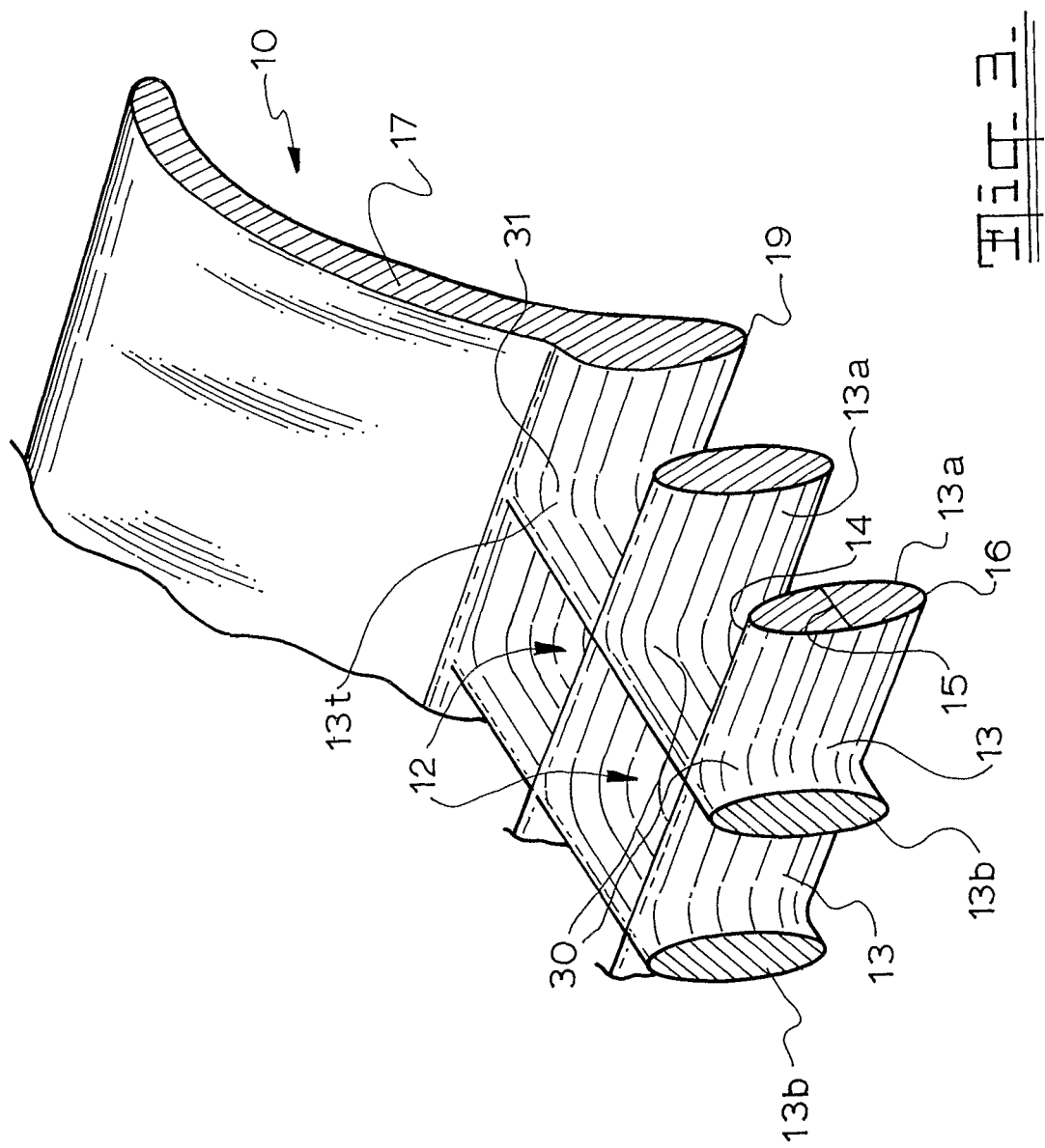
FIG. 3 shows a fragmentary perspective sectional view of a portion of a container component according to the invention.

As shown in FIG. 2 which shows a known construction of tray, and as shown in FIG. 3 which shows a tray embodying the present invention, the perforations 12 are defined by perforation walls 13. Each wall 13 in vertical cross-section is elliptical with the major axis vertical so as to commence at a top point 14, widens in a downwards direction to a maximum width 15 corresponding to the minor axis of the ellipse, and then narrows to a bottom point 16. The maximum width 15 is less than the distance from the top point 14 to the bottom point 16, i.e. the major axis. In FIGS. 1 and 3, the width 15 is less than half the distance from point 14 to point 16.

With this shape of the walls 13, the cumulative area of the perforations 12 in plan view can be maximised for flow of water or steam through the perforations. The narrowing of the wall shape from the width 15 downwardly to the bottom point 16 enables much of the water directed upwardly in a washer against the tray 10 to be deflected into the perforations 12 so that most of the water being directed upwardly can continue to flow upwardly through the perforations 12 to reach articles within the tray 10 even if the water first impinges on the walls 13.

As seen in FIG. 1, the bottom points 16 of the tray 10 define a bottom plane 18 and the bottom edge 19 of the side wall 17 meets but does not extend below this plane 18. Also, the perforation walls 13 and perforations 12 are provided across the entire area of the base 11 so that the bottom edge 19 of the side wall 17 presents only the same area in bottom plan view as a perforation wall 13. This enables articles in the tray 10, even if they are located at one side against a side wall 17, to be reached and contacted by cleaning fluid passing upwardly or downwardly through the container.

The same functional features are provided by the lid 20 so that the top points 24 of the perforation walls 23 define a plane 28 and the side wall 27 at its top edge 29 does not project above this plane 28. This construction enables containers comprising tray 10 and lid 20 as shown in FIG. 1 to be stacked one on top of each other with contact points being restricted to the bottom points 16 of tray 10 meeting and resting on top points 24 of a lid 20. This minimises the contact surface areas between stacked containers to minimise obstruction to flow of cleaning fluid through the stacked containers and also to minimise areas where moisture could collect at the areas of contact.

In the tray shown in FIG. 2 which is known, the perforation walls 13 intersect each other forming internal corners 30 which in horizontal cross section will form right angles. Such corners 30 can provide locations for debris, blood, or other deposits to lodge and such deposits will be more difficult to remove during the cleaning process. Likewise the corners 31 formed where the walls 13 meet with the side wall 17 form sharp internal angles more likely to be the sites of deposits.

As shown in FIGS. 3 to 6, the container component according to the present invention has perforation walls 13 including longitudinal perforation walls 13a extending in a first direction and transverse perforation walls 13b extending in a different second direction.

Figure 4:
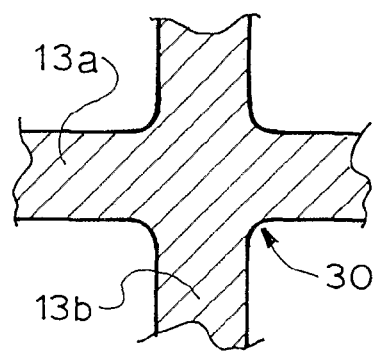
FIG. 4 shows a cross section through an intersection of walls at the widest part of the vertical cross sectional shape.
Figure 5:
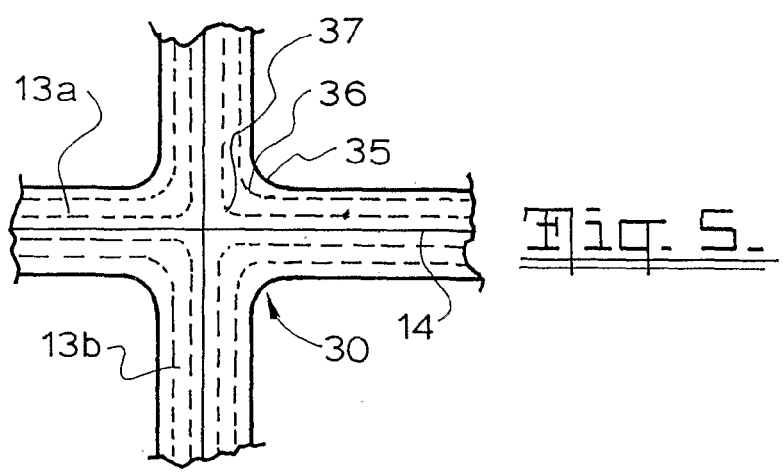
FIG. 5 shows a plan view of an intersection of walls with contour lines indicated so as to show the curvature at the internal corners of the perforations.

The term "longitudinal" is arbitrary and does not necessarily signify that the tray is longer in the direction of the walls 13a. The longitudinal and transverse perforation walls 13a, 13b meet at intersections which define corners 30 of the perforations 12. The intersections as best shown in FIGS. 4 and 5 in plan view or in horizontal cross section are of generally cruciform shape, which in the illustrated embodiments have the walls 13a, 13b meeting at right angles, but other angles of intersection are possible. The internal corners 30 are smoothly rounded so that there is no sharp internal angle formed where the longitudinal and transverse perforation walls 13a, 13b meet.

Figure 6:
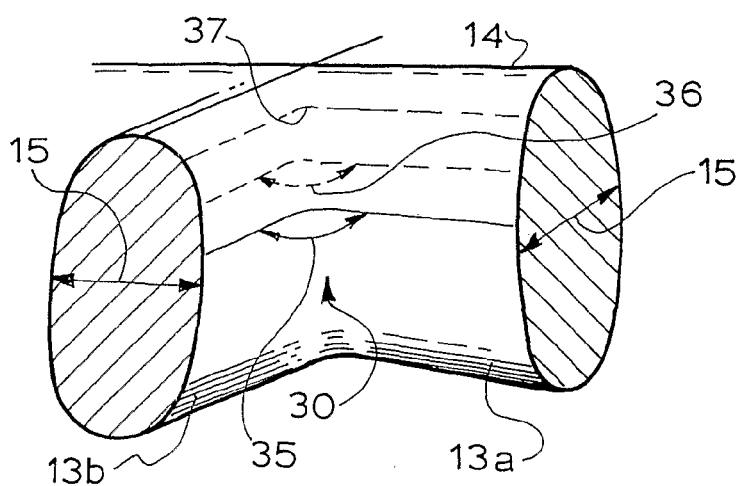
FIG. 6 is a detailed fragmentary perspective sectional view of the intersection of two perforation walls.

The radius of curvature of each internal corner 30 as shown in FIGS. 5 and 6 progressively increases in successive horizontal cross sections through the respective intersections starting from the cross sections near the tops 14 of the walls and progressing towards cross sections approaching and at the maximum width 15 of the walls. The curvature of the internal corners 30 in the horizontal plane where the walls reach their maximum width at 15 is at a maximum and therefore is greater than the curvature of the internal corners 30 of the perforations at any other horizontal cross section. This can be seen with the contour lines indicated in FIGS. 5 and 6 on the surfaces of the walls 13a, 13b including particularly contour line 35 at the maximum width 15, and contour line 36 at a horizontal section closer to the top 14 which has a smaller radius of curvature. At the internal corner 30, contour line 37, closer yet to the top 14 and having a yet smaller radius of curvature at the corner 30. The radius of curvature at the contour line 35 within the corner 30 may be for example about 1 mm or greater. The smooth rounding of the internal corners 30 of the intersections substantially reduces the likelihood that debris, blood, or other deposits will form at the internal corners 30 compared to the prior art and, if there are such deposits, the cleaning and/or sterilising operation has a substantially greater effectiveness in dislodging and removing and/or sterilising any such deposits that may be found in the corners 30.

The preferred container component according to the embodiment of the invention shown in FIGS. 1 and 3 has a plurality of side portions 17 around the perimeter of the base 11. The perforations 12 in the base are provided over substantial the entire surface area out to the perimeter of the base where the side portions 17 are located so that the instruments or other articles to be cleaned are located by the side portions 17 entirely in the perimeter of the base 11 where the perforations are provided. The tray 10 can have an open top 20 through which cleaning fluid can flow. The perforation walls 13a, 13b have terminal ends 13t which meet and join with the side portions 17. A horizontal cross section through each meeting of the terminal end 13t of a perforation wall 13 with the side portion 17 is generally of T-shape and the internal corners 31 of the T-shape are smoothly rounded in the same way as internal corners 30 so that there is no sharp internal angle formed where the perforation wall 13 meets the side portion 17.

Figure 7:
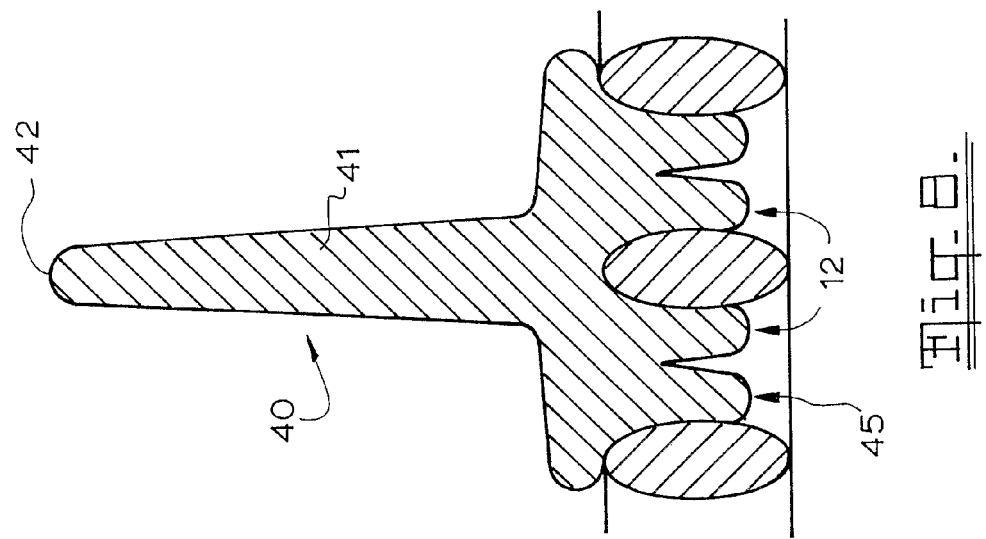
FIG. 7 is a cross section through one possible configuration of a support for instruments or articles to be carried in the container component for cleaning.
Figure 8:
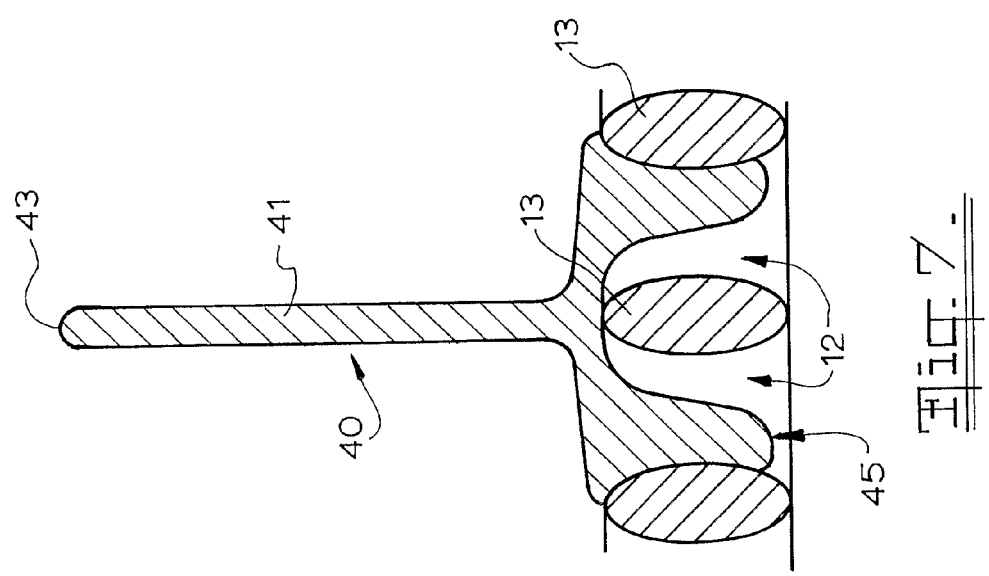
FIG. 8 is a cross section through another possible configuration of a support for instruments or articles to be carried in the container component for cleaning.

To support instruments or other articles, particularly delicate and/or expensive articles such as surgical instruments, endoscopic apparatus and the like, there may be provided article supports 40 projecting up above the base 11. As shown in FIGS. 7 and 8, each article support 40 can be in the form of an upright projection 41 mounted to the base by a resilient formation 45 which fits with and is retained within one or more perforations 12. The upright projection 41 may be in the form of an elongated web having a top edge 43 which is narrow in cross section so that articles resting on the top edge 43 meet with essentially a point contact. If desired, there may be concavities such as notches formed at spaced locations along the top edge 43 to more positively locate and retain articles such as delicate or expensive medical instruments. The formations 45 are shown as complementary in shape to perforations 12 and the supports 40, and more particularly the formations 45 may be made of a resilient material such as silicone rubber so that the support can be fitted to and securely retained in position in use. The use of silicon rubber or similar soft material can enable users of the tray to create customised locating concavities or notches in the top edges 43 of the supports 40 by cutting the notches using a razor or the like and thus create a support for different shapes and sizes of instruments. Multiple formations 45 would be provided along an elongated article support 40 with the spacing between successive formations 45 exactly corresponding to the spacing between perforations 12.

In the preferred embodiment or construction of the base of a tray for supporting instruments or other articles to be cleaned or sterilised, the spacing between adjacent parallel longitudinal perforation walls is preferably equal to the spacing between adjacent parallel transverse perforation walls. In this preferred embodiment, the perforations are substantially square in plan view (except for the smoothly rounded corners of the perforations). This preferred arrangement with the dimensions of the mesh formed by the longitudinal and transverse perforation walls being the same in the direction of a longitudinal X axis and a transverse Y axis enables article supports 40 to be fitted to the base 11 either extending transverse relative to the tray or longitudinally along the tray. This enables the arrangement and configuration of article supports 40 anywhere on the tray to suit the instruments or other articles that the tray may need to accommodate for a cleaning or sterilising operation. The article supports can be removed and relocated in different positions to support different instruments or other articles as required. It can also be appreciated that the article supports 40, particularly supports which are elongated, can form dividers separating the space within the tray into compartments for better organisation of articles to be cleaned or sterilised.

It will be seen that the container component, whether it be a tray or lid or cassette comprising a tray and lid, according to the present invention enables articles to be effectively reached by cleaning fluid, such as washing liquid in a washer or steam in an autoclave with reduced risk of debris, blood or other deposits collecting in corners of perforations or, if there are such deposits, the invention improves the effectiveness in removal during cleaning and sterilising. The cleaning fluid can also be peroxide gas or any other gas sterilant or oxidising gas. Also the cleaning fluid may be liquid, gaseous or plasma state. Apart from using high temperature or pressure sterilising operations such as an autoclave, the container component may be used in microwave sterilisation processes.

The method of cleaning or sterilising articles according to the second aspect of the invention can be readily understood from the preceding detailed description of the preferred embodiment of the container component. In particular, it can readily be understood how, according to the method of the second aspect of the invention, articles to be cleaned or sterilised are located within the container or container component so that the washing fluid or sterilising fluid effectively reaches the articles and there is reduced risk of debris, blood or other deposits collecting in corners of perforations with resulting higher risk of transfer to or contamination of the articles being cleaned or sterilised because, if there are such deposits, the particular construction of the perforations of the container component improve the effectiveness in removal of deposits during the cleaning or sterilising method of the invention.

The manufacture of the container component according to the first aspect of present invention, or used in the method according to the second aspect of the invention, is preferably performed by a moulding process, particularly an injection moulding process. The moulding of the container component without sharp corners for holding or retaining contaminants produces a substantially improved product compared a prior known fabrication process in which stainless steel wires are welded within a frame to form a mesh to receive instruments or other articles to be washed or sterilised. Such a fabrication process cannot achieve the objectives of preferred embodiments of the present invention in substantially eliminating corners within the container component. The manufacture of the dies used to form the mould for manufacture of the container component can be carried out by a suitably programmed CNC machine. The die cutting tools used to form the die cavities for the perforation walls can be hemi-spheroidal in shape, and more particularly hemi-ellipsoidal in shape, so as to thereby form the elliptical cross section of the perforation walls. To form the rounded corners at each intersection of the perforation walls, the cutting tool will be traversed around the corners from a transverse wall forming cavity to the intersecting longitudinal wall forming cavity, such traversal being controlled by the CNC machine. Different cutting tools may need to be used to form the different radii of curvature around the internal corners as herein described.

It is to be understood that various alterations, modifications and/or additions may be made to the features of the possible and preferred embodiment(s) of the invention as herein described and claimed without departing from the spirit and scope of the invention.

The invention claimed is:

1. A tray composed of moulded plastics material for enabling cleaning of articles located within the tray by fluid flow through the tray, comprising:

a tray base, the tray base having perforations provided over substantially the entire area where the articles are in use located and through which the cleaning fluid can flow, a plurality of side portions being located around the perimeter of the tray base, the perforations in the tray base being provided over substantially the entire surface area out to the perimeter where the side portions are located, so that the articles to be cleaned are located by the side portions entirely within the perimeter of the tray base where the perforations are provided, an open top through which the cleaning fluid can flow, wherein the perforations in the tray base are defined by perforation walls, each of the walls in vertical cross section having a narrow top, widening in a downwards direction to a maximum width and then narrowing again to a narrow bottom, the maximum width being less than the distance from the top to the bottom, the perforation walls include longitudinal perforation walls extending in a first direction and transverse perforation walls extending in a different second direction so that the longitudinal and transverse perforation walls meet at intersections defining internal corners of the perforations, the internal corners are smoothly rounded so that there are no sharp internal angles formed where the longitudinal and transverse perforation walls meet;

the perforation walls have terminal ends which meet and join with the side portions, and a horizontal cross-section through each meeting of the terminal end of a perforation wall with the side portion is generally of T-shape and internal corners of the T-shape are smoothly rounded so that there is no sharp internal angle formed where the perforation wall meets with the side portion.

2. The tray of claim 1, wherein the radius of curvature of each internal corner progressively increases in successive horizontal cross-sections through the respective intersections starting from cross sections near the tops of the walls and progressing towards cross sections approaching and at the maximum width of the walls.

3. The tray of claim 1, wherein the curvature of the internal corners of the perforations in the horizontal plane where the walls reach their maximum width is greater than the curvature of the internal corners of the perforations at any other horizontal cross-section.

4. The tray of claim 1, wherein each intersection in any one of multiple horizontal cross-sections therethrough is of generally cruciform shape.

5. The tray of claim 1, wherein each of the internal corners of the perforations in the horizontal plane where the walls reach their maximum width has a radius of curvature of about 1 mm or greater.

6. A method of cleaning or sterilising articles comprising the steps of:

providing a tray composed of moulded plastics material for receiving the articles during the cleaning or sterilising process, the tray comprising a tray base and a plurality of side portions being located around the perimeter of the tray base, the tray base having perforations, and the perforations in the tray base being provided over substantially the entire surface area out to the perimeter where the side portions are located;

locating the articles to be cleaned or sterilised within the tray so that they are located by the side portions entirely within an area where the tray base has the perforations provided therein; and causing a cleaning or sterilising fluid to flow past the articles within the tray including passing through the perforations of the tray base throughout substantially the entire area where the articles are located, wherein the perforations in the tray base are defined by perforation walls, each of the walls in vertical cross section having a narrow top, widening in a downwards direction to a maximum width and then narrowing again to a narrow bottom, the maximum width being less than the distance from the top to the bottom, the perforation walls include longitudinal perforation walls extending in a first direction and transverse perforation walls extending in a different second direction so that the longitudinal and transverse perforation walls meet at intersections defining corners of the perforations, the internal corners are smoothly rounded so that there is no sharp internal angle formed where the longitudinal and transverse perforation walls meet, the perforation walls have terminal ends which meet and join with the sides portions, and a horizontal cross-section through each meeting of the terminal end of a perforation wall with the side portion is generally of T-shape and the internal corners of the T-shape are smoothly rounded so that there is no sharp internal angle formed where the perforation wall meets with the side portion.

\* \* \* \* \*